United States Patent [19]

Mendiratta

[11] 4,147,732

[45] Apr. 3, 1979

[54] PROCESS FOR PRODUCING PENTACHLORO-NITROBENZENE

[75] Inventor: Sudhir K. Mendiratta, Cleveland, Tenn.

[73] Assignee: Olin Corporation, New Haven, Conn.

[21] Appl. No.: 881,272

[22] Filed: Feb. 27, 1978

[51] Int. Cl.² .............................................. C07C 79/12
[52] U.S. Cl. .................................................... 260/646
[58] Field of Search ........................................ 260/646

[56] References Cited

U.S. PATENT DOCUMENTS

| | | | |
|---|---|---|---|
| 3,026,358 | 3/1962 | Lojewski | 260/646 |
| 3,984,487 | 10/1976 | Watts, Jr. et al. | 260/646 |
| 4,026,955 | 5/1977 | Breaux et al. | 260/646 |
| 4,057,950 | 11/1977 | Gay | 260/646 |

*Primary Examiner*—Leland A. Sebastian
*Attorney, Agent, or Firm*—William A. Simons; Thomas P. O'Day

[57] ABSTRACT

An improvement is disclosed in the preparation of pentachloronitrobenzene by the nitration of pentachlorobenzene. The improvement, which is primarily aimed at reducing the residual level of the undesirable starting material, pentachlorobenzene, in the product, includes a two-stage reactant mixing step wherein the pentachlorobenzene is first mixed with sulfuric acid and then concentrated nitric acid is added to this mixture.

12 Claims, No Drawings

PROCESS FOR PRODUCING PENTACHLORO-NITROBENZENE

BACKGROUND OF THE INVENTION

1. Field of the Invention

This invention relates to an improved process for producing pentachloronitrobenzene by the nitration of pentachlorobenzene with concentrated nitric acid.

2. Description of the Prior Art

Pentachloronitrobenzene (sometimes referred to herein as PCNB) is widely used today as a soil fungicide. It is particularly effective in controlling plant diseases caused by botrytis, fusarium, rhizoctonia and anthracnose. However, some commercial products of PCNB have been questioned on environmental grounds because of the presence of relatively large amounts of two comtaminants contained therein. These chemicals, pentachlorobenzene (sometimes referred to herein as PENTA) and hexachlorobenzene (sometimes referred to herein as HCB), have been found to bioaccumulate in the fatty tissue of animals. Therefore, their presence in this desirable soil fungicide may cause a health hazard. For example, foodstuffs produced from soil which has been treated with quantities of impure fungicide may have PENTA and HCB leached into them and, thus, these impurities may accumulate in humans when they are later eaten. Also, cattle and other livestock that graze on treated grass or other pastures or grains may accumulate undesirable amounts of these impurities. And, furthermore, the farmer, when applying PCNB to soil, may breathe in significant quantities of these impurities.

Several methods are now known for the preparation of PCNB. Those of significance to the process described herein involve the nitration of pentachlorobenzene with mixed nitration acid, which consists essentially of a mixture of nitric and sulfuric acids.

In particular, U.S. Pat. No. 4,026,955, issued on May 31, 1977 to Breaux, Newman and Quinnett, teaches one such process. In this patent, it is disclosed that PCNB having reduced HCB content can be produced by a process wherein, first, pentachlorobenzene and mixed nitration acid are mixed together at an initial reaction temperature in the range of 100°–120° C. This resulting reaction mixture is then heated to an intermediate temperature in the range from 130° C. up to the melting point of PCNB and this reaction temperature is maintained for a time period sufficient to deplete the nitric acid concentration to a value of not more than 1% by weight of the reaction mixture. And, then, this reaction mixture is heated to a temperature in the range of 142° C. to 160° C. to form a melt and, finally, this melt is cooled to recrystallize the PCNB product.

Furthermore, U.S. patent application Ser. No. 826,603, filed on Aug. 22, 1977 by Walter Gay, teaches a process similar to that of Breaux et al. In that patent application, it is disclosed that the HCB formation may be substantially reduced by reacting any residual nitric acid with HCl immediately before the above-mentioned melt-forming step occuring in the temperature range of about 142° C. to about 160° C.

While the processes disclosed by these two references represent significant advances in producing relatively high purity PCNB, more recent research has shown that PENTA impurity level can be further substantially lowered by the process of the present invention.

BRIEF SUMMARY OF THE INVENTION

The present invention is directed to a process for producing pentachloronitrobenzene comprising
(a) mixing together sulfuric acid and pentachlorobenzene;
(b) mixing the resulting mixture with concentrated nitric acid at a temperature of from about 100° C. to about 120° C., said nitric acid being in molar excess of said pentachlorobenzene and the weight ratio of said sulfuric acid to said nitric acid being at least about 3:1;
(c) the resulting reaction mixture is heated to a temperature in the range of about 130° C. to about 140° C. and is maintained within this temperature range for a period of time which is no longer than is necessary for the conversion of pentachlorobenzene to pentachloronitrobenzene to be substantially complete;
(d) the reaction mixture is then heated to a temperature in the range of about 142° C. to about 160° C. to form a melt of pentachloronitrobenzene; and,
(e) the reaction mixture is then cooled to recrystallize the melted pentachloronitrobenzene.

DETAILED DESCRIPTION

The process of the present invention is an improvement upon the processes for producing PCNB disclosed in the above-cited U.S. Pat. No. 4,026,955 and U.S. patent application Ser. No. 826,603, both of which are incorporated by reference herein in their entirety. As discussed above, the Breaux et al. patent described a process for producing a highly pure PCNB product by reacting PENTA with a mixed nitration acid, wherein several reaction stages of differing temperatures were utilized. Also, as mentioned in that patent, it was found that the formation of the HCB impurity was a temperature-related phenomenon and a dramatic increase in HCB formation occurs in a mixed acid system at or above temperatures of 138°–142° C. Furthermore, that patent stated that when nitric acid concentration was depleted to a value of 1% by weight or less of the liquid fraction of the slurry prior to raising the temperature above the melting point of PCNB, the rate of hexachlorobenzene formation during the subsequent melting step undergoes a dramatic decrease. However, while this patented process produced an improved PCNB product having a low HCB content, more recent research found that the HCB content could be further lowered by practicing the improvements described in the Gay patent application. For instance, it was found that HCB content could be further controlled or minimized if the presence of any excess nitric acid (i.e., amounts even less than 1% by weight of the reaction mixture) were eliminated before the melt-forming step at 142°–160° C. This nitric acid elimination was accomplished simply by reducing the remaining nitric acid with HCl. However, while these two improved processes were mainly concerned with lowering HCB impurity level, the PCNB products produced by both processes still contained some unreacted PENTA in the final product. The presently described invention, therefore, is a further improvement upon these two processes in that it is primarily directed towards lowering or minimizing the amount of PENTA in the PCNB product.

Accordingly, the first step of the present process is to mix sulfuric acid with pentachlorobenzene. This mixing step can be accomplished by any conventional method with or without agitation. Upon mixing, there is no discernible reaction between the PENTA and $H_2SO_4$ and the PENTA, if solid, merely dissolves in the $H_2SO_4$. The pentachlorobenzene employed herein as a reactant can be obtained from any conventionally available source. For example, it may be prepared commercially by chlorinating benzene, mono-, di-, tri-, or tetrachlorobenzene or mixtures of any of these and then subjecting the resulting reaction mixture to any conventional recovery means, for example, distillation, in order to recover the pentachlorobenzene. The purity of the pentachlorobenzene is not a critical factor of the present process. However, it is preferred that the pentachlorobenzene be as pure as possible. It is important that it be substantially free of hexachlorobenzene so that the present process will not pass along appreciable amounts of this impurity to the PCNB.

The sulfuric acid can be obtained from any commercial source and preferably is in concentrated form containing at least 85% by weight $H_2SO_4$. Also, oleum (i.e., concentrated sulfuric acid containing varying amounts of sulfuric trioxide) may be substituted for sulfuric acid. Sufficient sulfuric acid should be present to act simultaneously as a solvent and catalyst and to take up water formed during the reaction. In particular, regarding its catalytic effect, it is known that the presence of sulfuric acid protonates the nitric acid and, thus, makes the nitric acid a more reactive species for the present invention. However, the relative amounts of sulfuric acid and pentachlorobenzene are dependent upon the amount of concentrated nitric acid as explained below.

After this mixing step is complete, the resulting mixture is further mixed with concentrated nitric acid at a temperature of from about 100° C. to about 120° C. This initial reaction temperature range is critical to the present invention. At mixing temperatures below about 100° C., production problems such as slow conversion of pentachlorobenzene, difficult temperature controls, and excess viscosity may be expected to be encountered. Moreover, at initial reaction temperatures above about 120° C., the formation of relatively substantial amounts of hexachlorobenzene occurs so that the resulting pentachloronitrobenzene product may be unacceptable because of undesirably high levels of hexachlorobenzene contained therein. Accordingly, it is necessary to conduct the addition or mixing of pentachlorobenzene, $H_2SO_4$, and concentrated nitric acid within the range of about 100° C. to about 120° C. Preferably, the mixing of these two reactants is carried out in the range of about 105° C. to about 115° C. Furthermore, the mixture of pentachlorobenzene and sulfuric acid may be added to the nitric acid or the nitric acid may be added to the resulting mixture as long as the proper temperature controls are maintained.

The concentrated nitric acid utilized in the present invention may be obtained from any commercial source. Pure or white concentrated nitric acid (i.e., less than about 1% by weight of $HNO_x$ where x is 1 or 2) is preferable although in some instances it may be acceptable to use brown fuming acid (i.e., nitric acid containing about 1% to about 5% by weight, of $HNO_x$ impurities where x is 1 or 2). The term "concentrated nitric acid" as employed in the present specification and claims means at least about 95%, preferably 98%, by weight of $HNO_3$.

Sufficient nitric acid should be utilized to provide a molar excess of nitric acid over the pentachlorobenzene. This molar excess will ensure substantially complete conversion (usually at least about 98% by weight) of the pentachlorobenzene. Besides, at the reaction temperatures employed herein, minor amounts of the nitric acid may be decomposed into volatile gases and thereby be unavailable for reaction. So preferably, at least about 25% molar excess of nitric acid should usually be employed to assure consistently high conversion of the pentachlorobenzene. More preferably, from about 40% to 100%, most preferably 50% to 75%, molar excess of nitric acid over pentachlorobenzene may be utilized. Thus, sufficient mixed nitration acid may be preferably utilized to provide at least about 1.25, more preferably about 1.4 to 2.0, most preferably about 1.5 to 1.75, moles of nitric acid per mole of pentachlorobenzene. Also, it is advantageous to use a weight ratio of sulfuric acid to nitric acid of at least about 3:1, preferably from about 3:1 to about 9:1, to insure the presence of sufficient sulfuric acid in order to carry out the above-noted functions.

This initial two-step mixing operation differs from the above-noted prior art processes which instead utilized a simple one-step mixing operation and a mixed nitration acid. As shown by the Examples below, the present two-step method substantially eliminates any residual pentachlorobenzene impurities in the final product. It is not exactly known why this occurs. However, it is now theorized that the prior art one-step mixing resulted in too much entrappment of PENTA in the solid PCNB product, even so that the further heating step in the range of 130° C. to about 140° C. will not allow all of the unreacted PENTA to become released from the solid product and thereafter react with the nitric acid. It is thought that the present two-step mixing minimizes the amount of PENTA entrappment in the solid product because the PENTA is already in solution when it is being reacted with the nitric acid.

During this mixing step, the reaction of pentachlorobenzene with nitric acid to form PCNB occurs almost simultaneously with their mixing together. The pentachloronitrobenzene formed by this reaction is a solid which normally falls to the bottom of the reaction mixture at the later stages of this first step. In this initial reaction step, it is believed 85-99% by weight of the pentachlorobenzene is converted. It has also been found that hexachlorobenzene is not formed to any significant degree during this early low temperature stage of the reaction.

The reaction of pentachlorobenzene with nitric acid is highly exothermic. In order to control the temperature of the reaction mixture during addition, it is necessary to add the two reactants together at a rate sufficient to maintain the temperature to within the above-stated initial temperature range. Normally, the addition step may generally take from about one to about five hours. Furthermore, external cooling may be provided for more rapid addition, but such cooling is ordinarily not necessary. Also, it may be desirable to employ known stirring or agitating means to keep the reactants well mixed and to also maintain proper temperature control.

After the addition or mixing of reactants at about 100°-120° C. is completed, the reaction mixture is heated to about 130° C. to about 140° C. and maintained in this temperature range for a period of time which is not greater than the time necessary for the conversion of pentachlorobenzene to pentachloronitrobenzene to be substantially completed (i.e., at least about 98% by weight of PENTA is converted to PCNB). Preferably, the reaction mixture is heated to about 133°-138° C.

This heating step is necessary to the present process because the solid pentachloronitrobenzene product formed in the prior mixing step will undergo partial melting and/or changes in crystal structure at these temperatures of about 130°-140° C. These physical changes, coupled with the increased reaction temperature, will cause any unreacted pentachlorobenzene entrapped in the solid pentachloronitrobenzene product to react with the nitric acid. Accordingly, the pentachlorobenzene that was not reacted in the mixing step is now substantially converted to pentachloronitrobenzene by this step. The final PCNB product will, thus, contain little or substantially none of the undesirable PENTA.

The maximum duration limit of this step is also an important feature of the present process. It has been found that hexachlorobenzene formation increases steadily with the passage of time at the reaction temperatures of this step, namely, about 130°-140° C. However, as explained above, this heating step must be maintained for a sufficient period of time in order to partially melt the solid PCNB product and thereby allow the exposed PENTA to react with nitric acid. Therefore, some hexachlorobenzene may be formed during this step. But, it is desirable to terminate this step as soon as possible so as to keep the formation of HCB to a minimum. Accordingly, it is an important feature of the present process not to allow this heating step to proceed for any longer period of time than is necessary for the conversion of PENTA to PCNB to be substantially complete. Allowing this heating step to be maintained any longer only causes the formation of HCB without any appreciable benefit to the process. A definite time period in minutes or hours cannot be generally given because this may vary with the types of equipment and/or procedures (e.g., heating with or without pressure) which may be utilized for carrying out this heating step on a commercial scale. However, this heating step is normally no more than about one hour long. The ratio of time to the conversion of PENTA to PCNB may be determined by simple experimentation whereby various samples are taken at various times after the beginning of this heating step and these samples are analyzed for the percentage of PENTA left unconverted. This step should be over before the percentage of PENTA remains unchanged for any appreciable length of time. Preferably, this heating step is held for a sufficient period of time which results in substantially complete conversion of PENTA to PCNB.

Furthermore, in a preferred embodiment of the present invention, the reaction time above about 130° C. can be minimized further by utilizing a two-stage heating step after the mixing step at 100°-120° C. In particular, this two-stage heating step is carried out by first heating to and maintaining the reaction mixture at a temperature within the range of about 121° C. to about 129° C., more preferably about 123°-127° C. Next, the reaction mixture is reheated to about 130°-140° C. and maintained at that range for a period of time no longer than is necessary to have substantially complete conversion of the pentachlorobenzene to pentachloronitrobenzene. The heating step at this lower temperature range of about 121°-129° C. will cause further conversion of the unreacted PENTA to PCNB. Thus, the amount of unconverted PENTA left in the reaction mixture after this heating at about 121°-129° C. will be less than if the reaction mixture is directly heated to about 130°-140° C. Moreover, the time for substantially complete conversion of PENTA to PCNB at this latter temperature range will be shorter, thereby minimizing the possibility of HCB formation in the reaction mixture. A purer PCNB product therefore may result.

After this heating step at about 130°-140° C., substantially all of the excess nitric acid still present in the reaction mixture may be preferably reacted with HCl. Normally, a sufficient quantity of HCl may be simply added to the reaction mixture. However, HCl may alternatively be generated in situ by adding a chlorine-containing salt such as sodium chloride to the reaction mixture. The chlorine-containing salt will be converted to HCl through a reaction with the $H_2SO_4$. The resulting HCl may then react with excess nitric acid in the reaction mixture. Therefore, the term "HCl" as employed in the specification and claims herein encompasses any and all means by which it is provided, including direct addition or in situ formation.

The reactions believed to be caused by the addition of HCl and its in situ generation in the reaction mixture are illustrated by equations (1), (2A), and (2B), respectively:

$$2HNO_3 + 4HCl \rightarrow N_2O_3 + 2Cl_2 + 3H_2O \tag{1}$$

$$4NaCl + 2H_2SO_4 \rightarrow 2Na_2SO_4 + 4HCl \tag{2A}$$

$$2HNO_3 + 4HCl \rightarrow N_2O_3 + 2Cl_2 + 3H_2O \tag{2B}$$

Further, the volatile gases $N_2O_3$ and $Cl_2$ may interact to form other volatile gases NOCl and $NO_2$ according to the reaction indicated by equation (3):

$$2N_2O_3 + Cl_2 \rightarrow 2NOCl + 2NO_2 \tag{3}$$

The destruction of the excess nitric acid with HCl has two beneficial effects on the present process. The first one is prevention of substantially any HCB formation in the subsequent melting step, as discussed below. The second is that the destruction of the nitric acid into volatile gases such as $N_2O_3$ and $Cl_2$ aids in the subsequent clean-up of spent sulfuric acid and reduces recovery costs.

If used, the amount of HCl added to the reaction mixture should be sufficient to react with substantially all of the nitric acid present therein, as shown in equations (1), (2A) and (2B). However, it should be noted that since most of the nitric acid has already been converted by reaction with the PENTA, only relatively small amounts of nitric acid are usually left in the reaction mixture. Thus, only relatively small amounts of HCl (e.g., 0.25-1.0 mole per mole of PCNB being formed) are needed for reaction with the excess nitric acid.

Other reducing agents of nitric acid besides HCl have been considered. For example, cupric sulfide, ferrous sulfate and oxalic acid have been employed but were found to give poor results. Furthermore, reducing agents such as sodium hydrosulfite, sodium thiosulfate and sodium hydrosulfide were found to give some acceptable destruction of excess nitric acid. However, these reducing agents have certain disadvantages associated with them. These disadvantages include the formation of malodorous gases, highly exothermic reactions and precipitation of free sulfur. The use of HCl, on the other hand, gave slightly endothermic reactions, produced easily workable products with nitric acid and is a readily available chemical.

Next, the reaction mixture is then heated to a temperature in the range of about 142° C. to about 160° C. This further heating step is necessary to completely melt the solid PCNB product formed in both the prior mixing and heating steps. This melt formation is desired in order to recover larger crystals of PCNB and to allow entrapped $H_2SO_4$ and other contaminants to escape from the solid product. Preferably, temperatures in the range of about 145° C. to about 155° C. are utilized.

The time duration for this melting step is not critical to the present process. The desired time could certainly vary and one having ordinary skill in the art could easily select the most appropriate time for each situation. In a preferred embodiment of the present invention, the time duration of this step is normally not much more than what is required to produce a complete melt of the PCNB product, approximately 0.25 to 1.0 hour.

After formation of this melt, the reaction mixture is cooled to recrystallize the PCNB contained in the reaction mixture. This cooling may be done by any conventional means such as by removing the heat source or employing the cooling jacket around the reaction mixture. Normally, dropping the temperature of the reaction mixture below about 100° C., preferably from about 20°–80° C., for a sufficient amount of time will result in recrystallization of PCNB product in excess of 95% by weight yields.

After the cooling step is completed, the solid pentachloronitrobenzene crystals in the reaction mixture may be recovered or subjected to further chemical reaction in the production of other chemicals. Product recovery can be achieved by any suitable technique such as any conventional liquid-solid separation means such as filtrating, cetrifuging, decanting and the like. Preferably, the solid crystal and the pentachloronitrobenzene product were recovered by filtering, followed by washing with a suitable solvent such as water to remove residuals. The recovered pentachloronitrobenzene is a highly pure product. Each of the levels of hexachlorobenzene and pentachlorobenzene is preferably less than 0.8%, more preferably less than 0.3%, by weight of the total pentachloronitrobenzene product.

The following examples and comparisons further illustrate the present invention. All parts and percentages are by weight unless otherwise expressly indicated.

EXAMPLE 1

Into a three-neck 750 ml flask equipped with a mechanical agitator, thermometer and condenser were charged 250 g of 99.7% pure granular pentachlorobenzene and 440 g of 92% sulfuric acid which was heated to 104°–108° C. by means of an electric heating mantle. The flask was then charged with 100 g of 99% pure concentrated nitric acid. This concentrated nitric acid was gradually added over a period of 0.83 hours while the reaction mixture was stirred and the temperature of the mixture maintained at 104°–108° C. Following this addition, the reaction mixture was heated to 125° C. for one hour followed by further heating at 135° C. The reaction mixture was heated again to raise the reaction temperature to above 145° C. and to form a liquid melt of pentachloronitrobenzene. The reaction mixture was maintained at this temperature for about 30 minutes. Next, the reaction mixture was cooled to 30°–70° C. by switching off the heating mantle and blowing cool air on the flask for about 30 minutes. The reaction mixture was then filtered by suction. The pentachloronitrobenzene product in the filter cake was washed twice with about 500 ml of distilled water each time. After drying at room temperature for 24 hours, the product was analyzed by Vapor Phase Chromatography (VPC). In this specific example, the product was of exceptional quality with an assay of 99.74% pentachloronitrobenzene, less than 0.01% pentachlorobenzene and 0.26% hexachlorobenzene.

EXAMPLE 2

The experiment of Example 1 was repeated except that the concentrated nitric acid was added over a period of 2.66 hours instead of 0.83 hours. The resulting product assay was 99.27% pentachloronitrobenzene, less than 0.01% pentachlorobenzene and 0.73% hexachlorobenzene.

EXAMPLE 3

The experiment of Example 1 was repeated except that the brown fuming nitric acid was added instead of concentrated pure nitric acid. The resulting product assay was 99.39% pentachloronitrobenzene, less than 0.01% pentachlorobenzene and 0.60% hexachlorobenzene.

COMPARISON 1

The experiment of Example 1 was repeated except that 540 g of mixed nitration acid containing 18.5% by weight concentrated pure nitric acid and 81.5% by weight sulfuric acid was added to 250 g of pentachlorobenzene for three hours instead of adding 100 g of concentrated pure nitric acid to a mixture of 250 g of pentachlorobenzene and 440 g of sulfuric acid for 0.83 hours. The resulting product assay was 99.12% pentachloronitrobenzene, 0.32% pentachlorobenzene and 0.48% hexachlorobenzene.

COMPARISON 2

The experiment of Comparison 1 was repeated except that mixed nitration acid was added for one hour instead of three hours. The resulting product assay was 99.00% pentachloronitrobenzene, 0.52% pentachlorobenzene and 0.46% hexachlorobenzene.

Table I

| Example or Comparison | Nitric Acid Quality | Add. Rate (hrs.) at 104–108° C. | Post Reaction (hrs.) at 125° C. | Post Reaction (hrs.) at 135° C. | VPC Product Assay (% by weight) HCB | VPC Product Assay (% by weight) PENTA | VPC Product Assay (% by weight) PCNB |
|---|---|---|---|---|---|---|---|
| E-1 | White Conc. | 0.83 hrs. | 1 hr. | 1 hr. | 0.26 | <0.1 | 99.74 |
| E-2 | White Conc. | 2.66 hrs. | 1 hr. | 1 hr. | 0.73 | <0.1 | 99.27 |
| E-3 | Brown Fuming | 0.83 hrs. | 1 hr. | 1 hr. | 0.60 | <0.1 | 99.39 |
| C-1 | White Conc. | 3.0 hrs. | 1 hr. | 1 hr. | 0.48 | 0.32 | 99.12 |
| C-2 | White Conc. | 1.0 hr. | 1 hr. | 1 hr. | 0.46 | 0.52 | 99.00 |

What is claimed is:

1. A process for producing pentachloronitrobenzene comprising:
   (a) mixing together sulfuric acid and pentachlorobenzene;

(b) mixing the resulting mixture with concentrated nitric acid at a temperature of from about 100° to about 120° C., said nitric acid being in molar excess of said pentachlorobenzene and the weight ratio of said sulfuric acid to said nitric acid being at least about 3:1;

(c) heating the resulting reaction mixture to a temperature in the range of about 130° C. to about 140° C. and maintaining said reaction mixture within said temperature range for a period of time which is no longer than is necessary for the conversion of pentachlorobenzene to pentachloronitrobenzene to be substantially complete;

(d) heating said reaction mixture to a temperature in the range of about 142° C. to about 160° C. to form a melt of pentachloronitrobenzene; and (e) cooling said reaction mixture to recrystallize the melted pentachloronitrobenzene.

2. The process of claim 1 wherein said reaction mixture is maintained at a temperature in the range of about 121° C. to about 129° C. after step (b) and before step (c).

3. The process of claim 1 wherein said heating step (c) is maintained for a sufficient amount of time in order to obtain substantially complete conversion of pentachlorobenzene to pentachloronitrobenzene.

4. The process of claim 1 wherein said nitric acid is utilized in at least about 25% molar excess over said pentachlorobenzene.

5. The process of claim 1 wherein HCl is added to said reaction mixture after step (c) and before step (d) in order to react with substantially all of the remaining unreacted nitric acid in said reaction mixture.

6. The process of claim 1 wherein the weight ratio of said sulfuric acid to said nitric acid is from about 3:1 to about 9:1.

7. The process of claim 6 wherein the molar ratio of said nitric acid to said pentachlorobenzene is in the range from about 1.4:1 to about 2.0:1.

8. The process of claim 7 wherein said reaction mixture is maintained at a temperature in the range of about 121° C. to about 129° C. after step (b) and before step (c).

9. The process of claim 8 wherein heating step (c) is maintained for a sufficient amount of time in order to obtain substantially complete conversion of pentachlorobenzene to pentachloronitrobenzene.

10. The process of claim 9 wherein said heating step (c) is carried out at a temperature in the range from about 133° C. to about 138° C.

11. The process of claim 10 wherein said mixing step (b) is carried out at a temperature in the range of about 105° C. to about 115° C.

12. The process of claim 11 wherein said concentrated nitric acid is pure concentrated nitric acid.

* * * * *